United States Patent
Saito et al.

(10) Patent No.: US 9,222,914 B2
(45) Date of Patent: Dec. 29, 2015

(54) MAGNETIC PROFILE MEASURING DEVICE AND METHOD FOR MEASURING MAGNETIC PROFILE FOR ALTERNATING-CURRENT MAGNETIC FIELD

(71) Applicant: AKITA UNIVERSITY, Akita-shi, Akita (JP)

(72) Inventors: Hitoshi Saito, Akita (JP); Satoru Yoshimura, Akita (JP)

(73) Assignee: AKITA UNIVERSITY, Akita-shi, Akita (JP)

( * ) Notice: Subject to any disclaimer, the term of this patent is extended or adjusted under 35 U.S.C. 154(b) by 45 days.

(21) Appl. No.: 14/347,417

(22) PCT Filed: Sep. 25, 2012

(86) PCT No.: PCT/JP2012/074600
§ 371 (c)(1),
(2) Date: Mar. 26, 2014

(87) PCT Pub. No.: WO2013/047538
PCT Pub. Date: Apr. 4, 2013

(65) Prior Publication Data
US 2014/0218016 A1    Aug. 7, 2014

(30) Foreign Application Priority Data

Sep. 26, 2011   (JP) ................... 2011-210009

(51) Int. Cl.
| | | |
|---|---|---|
| G01R 33/12 | (2006.01) | |
| G01N 27/72 | (2006.01) | |
| G01Q 30/04 | (2010.01) | |
| G01Q 60/54 | (2010.01) | |
| G01R 33/038 | (2006.01) | |
| B82Y 35/00 | (2011.01) | |

(52) U.S. Cl.
CPC .............. *G01N 27/725* (2013.01); *G01Q 30/04* (2013.01); *G01Q 60/54* (2013.01); *G01R 33/0385* (2013.01); *B82Y 35/00* (2013.01)

(58) Field of Classification Search
CPC ............ B25J 7/00; B25J 15/12; B82Y 35/00; G01B 5/25; G02B 21/32; G01Q 60/38; G01Q 60/54; G01Q 80/00; G01Q 10/02; G01Q 10/04; G01Q 70/08; G01Q 30/04; G01Q 70/16; G01Q 10/06; G01R 27/02; G01R 27/08; G01R 33/0385; G01N 27/725
USPC ............ 324/210, 244, 228, 658–716; 73/105; 850/40, 52, 56, 57, 62, 63
See application file for complete search history.

(56) References Cited

U.S. PATENT DOCUMENTS

| | | | | |
|---|---|---|---|---|
| 2001/0030536 A1* | 10/2001 | Abe | ............................... | 324/244 |
| 2001/0038282 A1* | 11/2001 | Abe | ............................... | 324/210 |
| 2002/0130658 A1* | 9/2002 | Abe | ............................... | 324/210 |

FOREIGN PATENT DOCUMENTS

| | | |
|---|---|---|
| JP | 2007-232596 A | 9/2007 |
| JP | 4769918 B1 | 9/2011 |
| WO | 2009/101991 A1 | 8/2009 |

OTHER PUBLICATIONS

International Search Report mailed Dec. 25, 2012; PCT/JP2012/074600.

*Primary Examiner* — Son Le
(74) *Attorney, Agent, or Firm* — Ladas & Parry LLP

(57) ABSTRACT

A magnetic profile measuring device which scans a space where an alternating-current magnetic field exists by a magnetized probe on a tip of a driven cantilever, detects vibration of the cantilever, and generates an image of magnetic field distribution of the space, the device including: the cantilever having the probe equipped on the tip thereof; a driver driving the cantilever; a vibration sensor detecting vibration of the probe wherein the driven vibration of the cantilever is frequency-modulated by the alternating-current magnetic field; a demodulator demodulating from a detection signal of the vibration sensor a magnetic signal corresponding to an alternating-current magnetic field; a scanning mechanism; a data storage storing an initial data for each coordinate of the space; a modified data generator recalling the initial data from the data storage and generating a plurality of data by modifying the phase of the initial data; and an image display device.

3 Claims, 10 Drawing Sheets

Fig. 8A
Fig. 8B
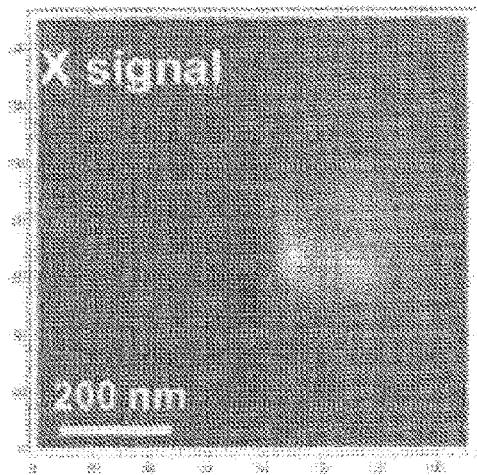
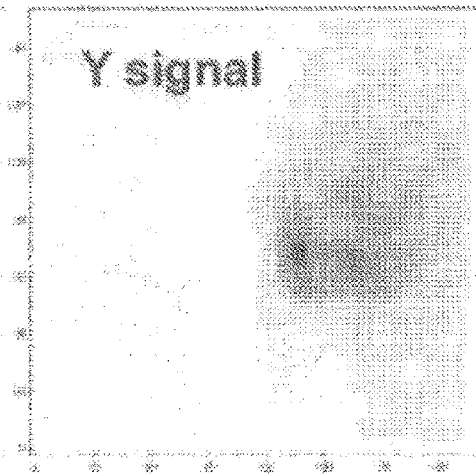

PRIOR ART

MAGNETIC PROFILE MEASURING DEVICE AND METHOD FOR MEASURING MAGNETIC PROFILE FOR ALTERNATING-CURRENT MAGNETIC FIELD

TECHNICAL FIELD

The present invention relates to a technique to measure a magnetic profile of a space where an alternating-current magnetic field exists or a magnetic profile of an alternating-current magnetic field generating device by scanning the space by means of a probe provided on a tip of a driven cantilever.

Specifically, the present invention relates to a magnetic profile measuring device and a method for measuring a magnetic profile which make it possible to obtain an image of magnetic field distribution (in specific, an image of perpendicular magnetic field distribution and/or an image of in-plane magnetic field distribution) whose phase is arbitrarily adjusted from an image data with its phase unchanged (initial data).

BACKGROUND ART

Conventionally, as a device to obtain a magnetic profile of an object to be measured, a magnetic force microscope (MFM) is known. MFM includes ones to observe a direct current magnetic field (DC magnetic field) and ones to observe an alternating-current magnetic field (AC magnetic field). Since the present invention is a technique related to MFM to observe an alternating-current magnetic field, a conventional technique of MFM to observe an alternating-current magnetic field will be hereinafter described.

FIG. 10 is a figure to explain a conventional magnetic profile measuring device 8 using a MFM (see Patent Document 1). The magnetic profile measuring device 8 includes a cantilever 81, and a magnetized probe 811 is provided on a tip of the cantilever 81.

This magnetic profile measuring device 8 can measure a magnetic profile (a state of magnetic field distribution) of a space where an alternating-current magnetic field generated by an alternating-current magnetic field generating device 88 exists. Also, the magnetic profile measuring device 8 can measure a magnetic profile of the alternating-current magnetic field generating device 88 itself (for example, magnetic property of a surface of a writing head of a hard disc drive).

In FIG. 10, the cantilever 81 is driven by a driver 82 at a resonant frequency of the cantilever or at a frequency close to the resonant frequency of the cantilever.

For example, driven frequency of the cantilever 81 can be around the resonant frequency of the cantilever 81 (for example, around 300 kHz). Here, a frequency of the alternating-current magnetic field generated by the alternating-current magnetic field generating device 88 can also be around the resonant frequency of the cantilever 81, in the same way as the driven frequency of the cantilever 81.

When the alternating-current magnetic field is applied to the cantilever 81, the probe 811 formed on the tip of the cantilever 81 is directly subjected to a magnetic driving force. This magnetic driving force directly changes amplitude and a phase of vibration of the cantilever 81 mechanically driven by the driver 82.

Therefore, when the driving frequency of the cantilever 81 is constant, the vibration of the probe 811 is modulated by both amplitude and phase, by the direct magnetic driving force from the alternating-current magnetic field.

It is possible to demodulate a magnetic signal corresponding to the magnetic force occurring between the probe 811 and the alternating-current magnetic field generating device 88 by detecting, for example optically, this vibration modulated by amplitude and phase.

A scanning mechanism 85 can scan the space where the alternating-current magnetic field exists by means of the probe 811. This makes it possible for the magnetic profile measuring device 8 to obtain a magnetic profile of the alternating-current magnetic field generating device 88 as an image of magnetic field distribution.

Referring to FIG. 10, an example in which the cantilever 81 is driven by the driver 82 at a resonant frequency of the cantilever or at a frequency close to the resonant frequency of the cantilever has been described. The frequency of the alternating-current magnetic field generated by the alternating-current magnetic field generating device 88 may be substantially different from the resonant frequency of the cantilever.

For example, when the resonant frequency of the cantilever 81 is around 300 kHz, it is possible to obtain the above described image of magnetic field distribution as long as the frequency of the alternating-current magnetic field generated by the alternating-current magnetic field generating device 81 is within the range of 1 to 100 kHz.

That is, when the probe 811 formed on the tip of the cantilever 81 is placed in the alternating-current magnetic field generated by the alternating-current magnetic field generating device 88, a non-resonant alternating-current magnetic force occurs between the probe 811 and the alternating-current magnetic field generating device 88.

However, this non-resonant alternating magnetic force cannot drive the cantilever 81 by itself, and therefore any signal of the alternating-current magnetic field cannot be obtained.

It is possible to detect the signal of the alternating-current magnetic field by driving the cantilever 81 by means of the driver 82 such as a piezoelectric element at a frequency around the resonant frequency of the cantilever while causing the non-resonant alternating magnetic force between the probe 811 and the alternating-current magnetic field generating device 88.

Meanwhile, when the cantilever 81 is driven at a frequency around the resonant frequency of the cantilever while causing the non-resonant alternating magnetic force between the probe 811 and the alternating-current magnetic field generating device 88, the cantilever 81 behaves as if its effective spring constant had been periodically changed. This apparent periodical change in the spring constant causes frequency modulation in the vibration of the cantilever 81.

The vibration of the cantilever 81 modulated by frequency can be detected for example optically by means of a vibration sensor 83 including a laser and a photodiode (PD). An alternating magnetic force signal demodulator 84 can take in the detection signal and demodulate the signal of the alternating magnetic force.

Since the scanning mechanism 85 can scan the space where the alternating-current magnetic field exists by means of the probe 811, the magnetic profile measuring device 8 can obtain the magnetic profile of the alternating-current magnetic field generating device 88 as an image of magnetic field distribution.

On the other hand, when the cantilever 81 is driven at a frequency different from the resonant frequency of the cantilever by means of a piezoelectric element or the like, amplitude modulation as well as frequency modulation occurs in the vibration of the cantilever 81.

By detecting for example optically this vibration modulated by frequency and amplitude to demodulate by frequency or by amplitude, it is possible to obtain a magnetic profile of the alternating-current magnetic field generating device as an image of magnetic field distribution.

As in the example described above, it is supposed that the frequency of the alternating-current magnetic field generated by the alternating-current magnetic field generating device 88 is greatly different from the resonant frequency of the cantilever 81 and a non-resonant alternating magnetic force occurs between the cantilever 81 and the alternating-current magnetic field generating device 88 in measuring the magnetic profile of the alternating-current magnetic field generating device 88. For example, when the alternating-current magnetic field generating device 88 includes a magnetic coil 881 and a signal generator 882, its magnetic profile is an alternating-current magnetic field generated by the magnetic coil 881.

When a phase of the alternating-current magnetic field is synchronized with (identical to) a phase of the signal generator 882, a lock-in amplifier 86 can obtain a magnetic field component perpendicular to a reference surface (for example, in a magnetic recording head of a hard disk drive, a sliding surface of the magnetic recording head) of the magnetic coil 88 (perpendicular magnetic field component $H_p$), referring to the synchronizing signal output from the signal generator 882.

In this case, the magnetic coil 881 of the alternating-current magnetic field generating device 88, if there is no delay in magnetization process of its magnetic material, generates the maximum perpendicular magnetic field when instantaneous value (absolute value) of output current of the signal generator 882 becomes maximum.

CITATION LIST

Patent Literature

Patent Document 1: WO 2009/101991

DISCLOSURE OF THE INVENTION

Problems to be Solved by the Invention

When the frequency of the alternating-current magnetic field generated by the alternating-current magnetic field generating device (for example, a magnetic recording head of a hard disk) is sufficiently lower than the resonant frequency of the cantilever 81, the magnetic profile of the alternating-current magnetic field generating device 88 is measured by means of the lock-in amplifier 86, taking output voltage of the signal generator 882 of the alternating-current magnetic field generating device 88 as a reference signal $V_{ref}$.

As described above, when the phase of the alternating-current magnetic field generated by the alternating-current magnetic field generating device 88 is synchronized with (identical to) the phase of the output voltage of the signal generator 882, it is possible to obtain a magnetic field component perpendicular to the reference surface (the sliding surface of the magnetic recording head) of the magnetic coil 881 (perpendicular magnetic field component) by means of the synchronizing signal output of the lock-in amplifier 86. In a case where there is no delay in the magnetization process of the magnetic material, the magnetic coil 881 detects the maximum perpendicular magnetic field when the current of the signal generator 882 takes a maximum value.

However, in measuring the magnetic profile, phase of the measurement signal may delay inside of an electric circuit of the signal generator 882, in signal lines, and inside of an electric circuit of the alternating magnetic force signal demodulator 84. Further, magnetization change of the magnetic material (such as a core of the magnetic coil) used for the alternating-current magnetic field generating device 88 may delay more than the change of the magnetic field, which results in a further delay in the phase.

In the output of the synchronized signal of the lock-in amplifier 86, phase delay adds an in-plane magnetic field component generated from a magnetization component of the magnetic material (such as a core of the magnetic coil) parallel to the reference surface of the magnetic coil 881 (in a case where a magnetic recording head is employed, a sliding head) to a perpendicular magnetic field component generated from a magnetization component perpendicular to the reference surface.

Therefore, the phase delay make it difficult to obtain only a magnetic field component generated from the magnetization component perpendicular to the reference surface of the magnetic coil 881 (to obtain a magnetic field where a magnetic field generated from a magnetization component parallel to the reference surface of the magnetic coil 881 of the magnetic material (such as a core of the magnetic coil) is not included).

An object of the present invention is, for an alternating-current magnetic field generating device, using an image data of magnetic field distribution obtained, to provide a technique of measuring a magnetic profile which makes it possible to obtain an image of magnetic field distribution that is generated only by either one of two magnetization components of a specimen orthogonal to each other (for example, in a magnetic coil, either a magnetization component perpendicular to its reference surface or a magnetization component parallel to the reference surface).

Further, another object of the present invention is to provide a measuring technique to continuously observe a time-dependent change of the perpendicular magnetic field component associated with a time-dependent change of magnetic moment of the alternating-current magnetic field generating device.

Means for Solving the Problems

For an alternating-current magnetic field generating device, the inventors of the present invention firstly has conceived of, in demodulating detection signal, separating the detection signal into two magnetic field components generated from two respective magnetizations of a specimen orthogonal to each other and thereby making images to generate an image of magnetic field distribution.

Then they have reached to the present invention by finding out that, if an image of magnetic field distribution is made by changing either or both phases of the two images, it is possible to obtain an image of a magnetic field according to either of two magnetization components orthogonal to each other described above, and it is also possible to continuously observe time-dependent change of the magnetic field caused by either or both of the two magnetization components orthogonal to each other described above associated with the time-dependent change of the magnetic moment of the alternating-current magnetic field generating device.

A magnetic profile measuring device of the present invention includes a following embodiment.

(1)

A magnetic profile measuring device which scans a space where an alternating-current magnetic field generated by an alternating-current magnetic field generating device exists by means of a magnetized probe on a tip of a driven cantilever, detects vibration of the cantilever, and generates an image of magnetic field distribution of the space where the alternating-current magnetic field exists based on results of the detection, the device including:

the cantilever wherein the probe is equipped on the tip of the cantilever;

a driver driving the cantilever at a resonant frequency of the cantilever or at a frequency close to the resonant frequency of the cantilever;

a vibration sensor detecting vibration of the probe caused by driven vibration of the cantilever being modulated by the alternating-current magnetic field either by frequency or by both frequency and amplitude;

a demodulator demodulating from a detection signal of the vibration sensor a magnetic signal which corresponds to an alternating-current magnetic field at the position of the probe, and detecting the demodulated magnetic signal as (A) two separate signal components having phase difference of 90° and being orthogonal to each other or as (B) amplitude and a phase of the magnetic field at the position of the probe;

a scanning mechanism scanning a space where the alternating-current magnetic field exists by means of the probe;

a data storage storing an initial data for each coordinate of the space wherein the initial data is (A) the two separate signal components orthogonal to each other or (B) the amplitude and phase of the magnetic field, and wherein the initial data is obtained by scanning the space where the alternating-current magnetic field exists by means of the scanning mechanism, and wherein the initial data is stored with the phase of the initial data unchanged;

a modified data generator recalling the initial data from the data storage and generating a plurality of data by modifying the phase of the initial data; and an image display device displaying an image of a magnetic field distribution based on data generated for each coordinate of the scanned space by the modified data generator.

Where the magnetic field at the position of the probe is represented by $$H_X + jH_Y = H_0 \exp(j\theta)$$

in X-Y complex plane (Gauss plane, see FIG. 1);
amplitude of the magnetic field at the position of the probe, $H_0$, is represented by $$H_0 = (H_X^2 + H_Y^2)^{1/2}$$

which is a distance from the origin in the X-Y complex plane;
the phase of the magnetic field at the position of the probe is represented by $$\theta = \tan^{-1}(H_Y/H_X)$$

which is an argument θ in the X-Y complex plane;
X-component of the magnetic field at the position of the probe is represented by $$H_X = H_0 \cos \theta$$

which is a component parallel to the X-axis; and
Y-component of the magnetic field at the position of the probe is represented by $$H_Y = H_0 \sin \theta$$

which is a component parallel to the Y-axis perpendicular to the X-axis, the demodulator may detect the demodulated signal as (A) data pair of the X-component and the Y-component ($H_X$, $H_Y$) or as (B) a data pair of amplitude and the phase ($H_0$, θ).

Further, the magnetic field at the position of the probe may be displayed on the image display device by generating an image of the X-component and/or the Y-component according to change in the argument θ.

a method for measuring a magnetic field of the present invention includes a following embodiment.

(2)

A method for measuring magnetic profile including scanning a space where an alternating-current magnetic field generated by an alternating-current magnetic field generating device exists by means of a magnetized probe on a tip of a driven cantilever, detecting vibration of the cantilever, and generating an image of magnetic field distribution of the space where the alternating-current magnetic field exists based on results of the detection, the method comprising the steps of:

driving the cantilever at a resonant frequency of the cantilever or at a frequency close to the resonant frequency of the cantilever, wherein the probe is equipped on the tip of the cantilever (S110);

modulating driven vibration of the cantilever by means of the alternating-current magnetic field either by frequency or by both frequency and amplitude (S120);

detecting vibration of the probe and demodulating from the detection signal a magnetic signal which corresponds to an alternating magnetic force occurring between the probe and the alternating-current magnetic field generating device (S130);

detecting the demodulated magnetic signal as (A) two separate signal components which have phase difference of 90° and are orthogonal to each other or as (B) amplitude and a phase of the magnetic field at the position of the probe (S140);

scanning the space where the alternating-current magnetic field exists by means of the probe (S150);

storing an initial data in a data storage for each coordinate of the space wherein the initial data is (A) the two separate signal components orthogonal to each other or (B) the amplitude and phase of the magnetic field, and wherein the initial data is stored with the phase of the initial data unchanged (S160);

recalling the initial data from the data storage and generating a plurality of data by modifying the phase of the initial data (S170);

displaying an image of a magnetic field distribution based on data generated by modifying the phase of the initial data, on a image display device (S180); and measuring the magnetic profile of the space where the alternating-current magnetic field generated by the alternating-current magnetic field generating device exists based on each image of magnetic field distribution displayed on the image display device (S190).

(3)

The method for measuring magnetic profile according to (2), comprising the steps of:

modifying the phase of the image of magnetic field distribution having the same phase as the phase of the initial data stored in the data storage, and thereby generating a plurality of images of magnetic field distribution which have different phases; and identifying among the plurality of images of magnetic field distribution an image of magnetic field distribution which has (X) maximum or minimum brightness of the image of magnetic field distribution of the space where the alternating-current magnetic field exists or (Y) maximum or minimum brightness difference of the image of magnetic field distribution of the space where the alternating-current magnetic field exists.

In the step of separating the demodulated magnetic signal into two separate signal components which have phase difference of 90° and orthogonal to each other (S140), where the magnetic field at the position of the probe is represented by $$H_X + jH_Y = H_0 \exp(j\theta)$$

in X-Y complex plane (Gauss plane, see FIG. 1); amplitude of the magnetic field at the position of the probe, $H_0$, is represented by $$H_0 = (H_X^1 + H_Y^2)^{1/2}$$

which is a distance from the origin in the X-Y complex plane; the phase of the magnetic field at the position of the probe is represented by $$\theta = \tan^{-1}(H_Y/H_X)$$

which is an argument θ in the X-Y complex plane; X-component of the magnetic field at the position of the probe is represented by $$H_X = H_0 \cos\theta$$

which is a component parallel to the X-axis; and Y-component of the magnetic field at the position of the probe is represented by $$H_Y = H_0 \sin\theta$$

which is a component parallel to the X-axis orthogonal to the X-axis, the demodulated magnetic signal may be detected as (A) a data pair of the X-component and the Y-component ($H_X$, $H_Y$) or as (B) a data pair of the amplitude and the phase ($H_0$, θ).

Effects of the Invention

According to the present invention, it is possible to obtain an image of magnetic field caused by either one of two magnetization components of a specimen orthogonal to each other (for example, an image of perpendicular magnetic field generated from an in-plane magnetization component parallel to a surface of the specimen), using the obtained image data of magnetic field distribution.

Also, it is possible to continuously observe a time-dependent change of the perpendicular magnetic field component associated with a time-dependent change of magnetic moment of a soft magnetic material (such as a core of the magnetic coil) of the alternating-current magnetic field generating device.

That is, in the present invention, since it is possible to obtain an image of magnetic field distribution whose phase is arbitrarily adjusted (in specific, an image of perpendicular magnetic field and/or an image of in-plane magnetic field), even when a phase delay occurs in the measurement signal from a voltage (or current) for driving the coil generated by the signal generator for example, it is possible to compensate this phase delay.

This makes it possible to detect a magnetic field at a measurement point with a phase of the magnetic field adjusted to a phase of magnetization of a generation source of the magnetic field (alternating-current magnetic field generating device). Also, regarding the alternating-current magnetic field generating device, it is possible to continuously observe a time-dependent change of the magnetic field component associated with a time-dependent change of the magnetic moment.

Specifically, the present invention makes it possible to measure a magnetic profile of a magnetic recording head of a hard disk drive, which also makes it possible to evaluate the magnetic recording head.

BRIEF DESCRIPTION OF THE DRAWINGS

FIG. 4 includes figures to explain detection of vibration modulated by frequency or both frequency and amplitude.

FIG. 5 includes figures to explain detection of vibration modulated by frequency.

FIG. 8A is an image of perpendicular magnetic field distribution having a phase of the initial data (initial value) stored in the data storage, and FIG. 8B is a figure to show an example of an image of perpendicular magnetic distribution having a phase difference of 90° from the image of perpendicular magnetic distribution of FIG. 8A;

MODES FOR CARRYING OUT THE INVENTION

Figure 1:
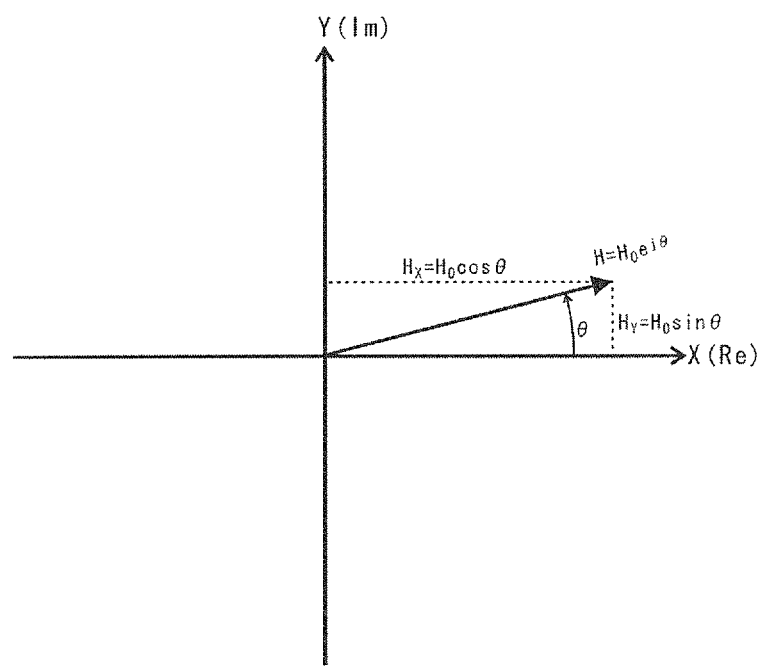
FIG. 1 is a figure to explain a mechanism of the present invention using X-Y complex plane.
Figure 2:
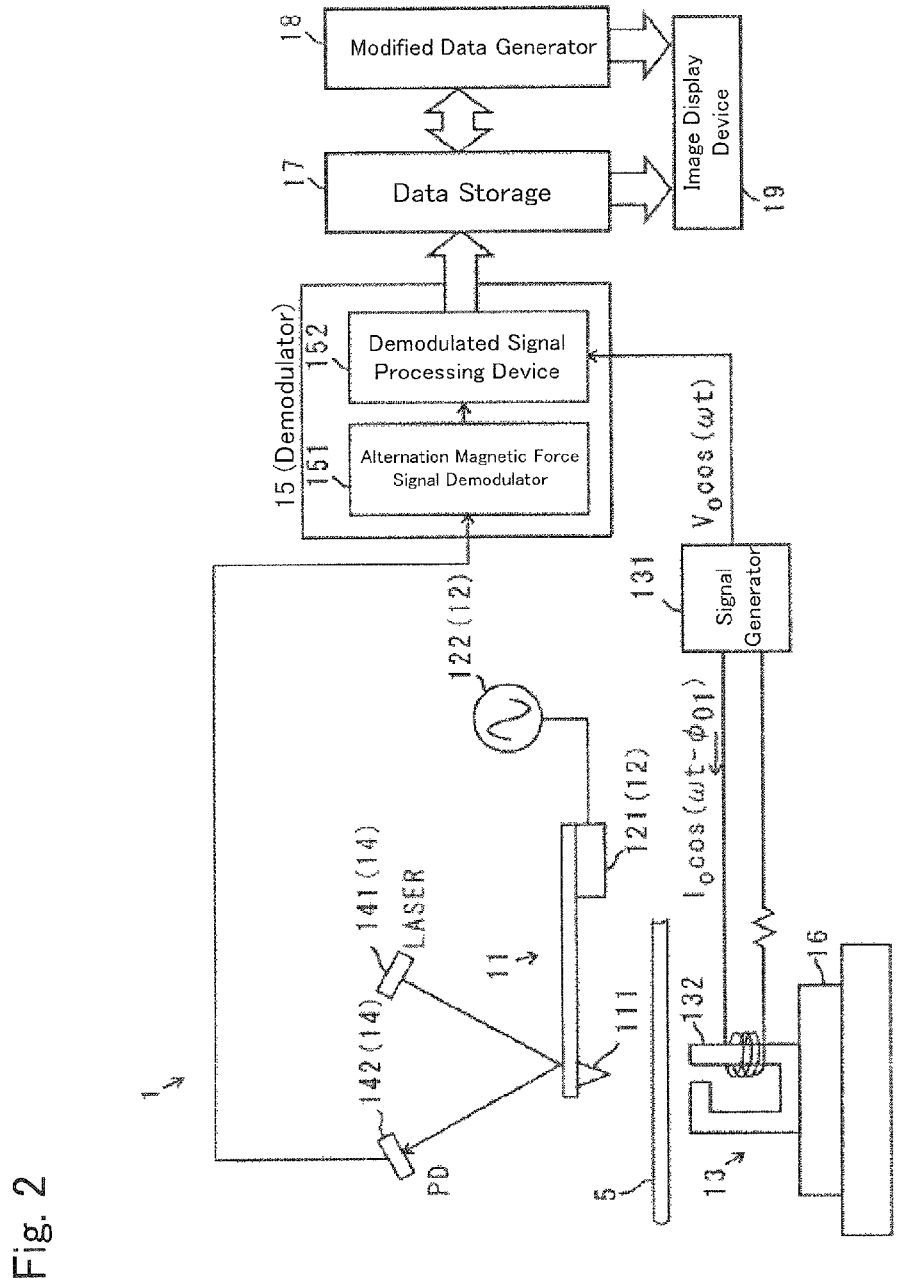
FIG. 2 is a figure to explain an embodiment of a magnetic profile measuring device of the present invention.

FIG. 2 is a figure to explain an embodiment of a magnetic profile measuring device of the present invention. In FIG. 2, a magnetic profile measuring device 1 includes a cantilever 11, a driver 12, a vibration sensor 13, a demodulator 14, a scanning mechanism 15, a data storage 16, a modified data generator 17, and an image display device 18. The magnetic profile measuring device 1 can scan a space where an alternating-current magnetic field generated by the alternating-current magnetic field generating device 5, by means of the magnetized probe 111 on a tip of the driven cantilever 11, detect vibration (stationary vibration) of the cantilever, and generate an image of magnetic field distribution of the space in which the alternating-current magnetic field exists based on results of the detection. Frequency of the magnetic field generated by the alternating-current magnetic generator 5 may be about 100 Hz to 1 kHz.

The cantilever 11 is equipped with the probe 111 on the tip. The probe 111 is formed in a conical shape, and has a film made of a material of a Fe—Pt based alloy on its surface. Magnetization of the probe 111 is get changed by the magnetic field generated by the alternating-current magnetic field generating device 5.

The driver 12 includes a piezoelectric element 121 and a power source 122. The power source 122 drives the piezoelectric element 121 and the cantilever 11 is driven by vibration of the piezoelectric element 121, whereby the driver 12 drives the cantilever 11 at a resonant frequency of the cantilever 11 or at a frequency close to the resonant cantilever of the cantilever 11. In this embodiment, frequency of the power source 122 may be 300 kHz.

By the alternating-current magnetic field generated by the alternating-current magnetic field generator 5, driven vibration of the cantilever 11 is modulated by frequency or by both frequency and amplitude.

The vibration sensor 13 detects vibration of the probe 111 generated by modulating the driven vibration of the cantilever 11 by frequency or by both frequency and amplitude by the alternating-current magnetic field.

In this embodiment, the vibration sensor includes a laser 131 and a photodiode (PD) 132, irradiates a laser beam from the laser 131 to the upper surface of the tip of the cantilever 11, detects the reflected light by means of the photodiode 132, and thereby detects the vibration of the probe 111.

By changing driving frequency of the driver 12, it is possible to generate frequency spectra having various patterns. As shown in FIG. 4, the vibration sensor 13 can detect the vibration modulated by frequency or by both frequency and amplitude, by adequately choosing the driving frequency. Also, as shown in FIG. 5, the vibration sensor 13 can detect the vibration modulated only by frequency, by adequately choosing the driving frequency.

Figure 4A:
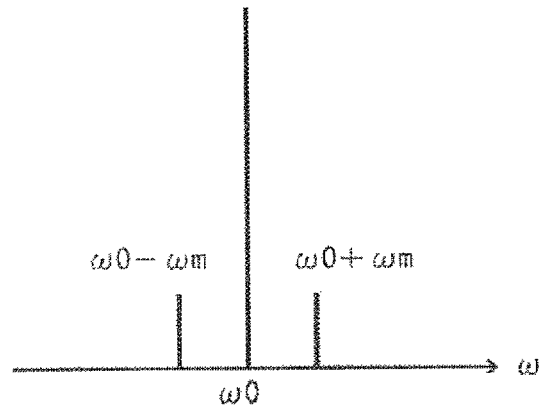
FIG. 4A is a spectrum diagram.

In the spectrum shown in FIG. 4A, the central spectrum is a central frequency of a driven vibration ($\omega_c$), and $\omega_c$ is same (or almost same) as the resonant frequency of the cantilever $\omega_0$. On both sides of $\omega_0$, two sidebands ($\omega_o-\omega_m$, $\omega_o+\omega_m$) of vibrations by the alternating-current magnetic field generated by the alternating-current magnetic field generating device 5 appear.

Figure 4B:
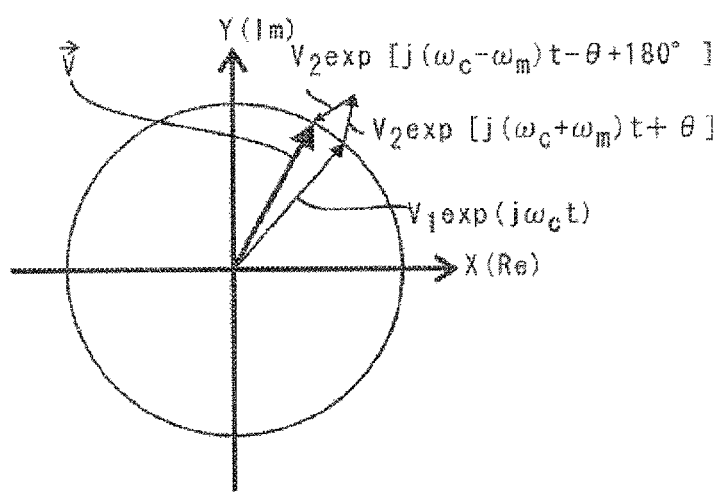
FIGS. 4B and 4C are vector diagrams to show relationship between a central frequency of driven vibration (central spectrum) and frequencies caused by an alternating-current magnetic field generated by an alternating-current magnetic field generating device (sidebands)
Figure 4C:
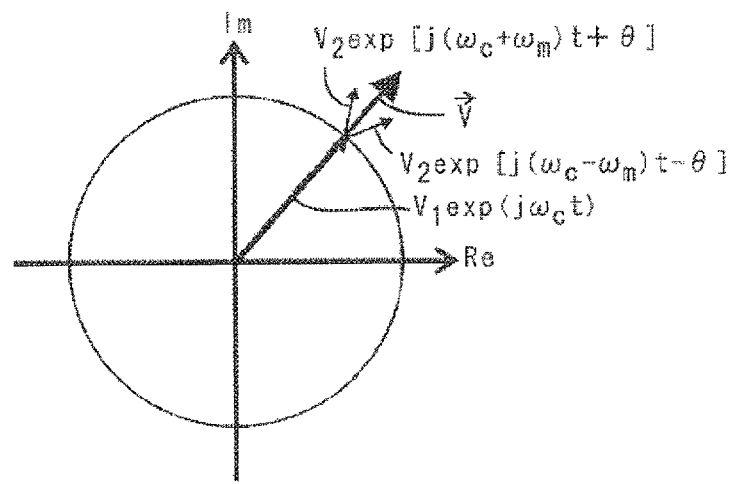

FIGS. 4B and 4C are vector diagrams showing relationship between the central frequency (central spectrum) of the driven vibration and frequencies (sidebands) by the alternating-current magnetic field generated by the alternating-current magnetic field generating device 5.

In FIG. 4B, the vector corresponding to the central spectrum is represented by $$V_1 \exp(j\omega_c t)$$

and the vectors of the two vibrations ($\omega_o-\omega_m$, $\omega_o+\omega_m$) corresponding to the sidebands are represented by $$V_2 \exp[j\{(\omega_c-\omega_m)t-\theta+180°\}]$$

$$V_2 \exp[j\{(\omega_c+\omega_m)t+\theta\}].$$

Synthetic vector V to be detected points a circumferential direction of the trajectory of the vector of the driven vibration (uniform speed rotation vector).

In this case, synthesis of the vectors of two vibrations corresponding to the sidebands changes only the frequency of the vector by the driven vibration. Therefore, when amplitudes of vibrations of the sidebands are small, the synthetic vector of the vector by the driven vibration and the vectors of the two vibrations corresponding to the sidebands has constant amplitude and only the frequency of the synthetic vector is changed.

In FIG. 4C, the vector corresponding to the central spectrum is represented by $$V_1 \exp(j\omega_c t)$$

and the vectors of the two vibrations ($\omega_o-\omega_m$, $\omega_o+\omega_m$) corresponding to the sidebands (each vector is a uniform speed rotation vector) are respectively represented by $$V_2 \exp[j\{(\omega_c-\omega_m)t-\theta\}]$$

$$V_2 \exp[j\{(\omega_c+\omega_m)t+\theta\}]$$

Synthetic vector V to be detected points the radial direction of the trajectory of the vector of the driven frequency (uniform speed rotation vector).

In this case, synthesis of the vectors of the two vibrations corresponding to the sidebands changes only the size of the vector of the driven vibration. Therefore, the synthetic vector of the vector of the driven vibration and the vectors of the two vibrations corresponding to the sidebands has a constant frequency and only the amplitude of the synthetic vector changes.

In a case where the frequency $\Omega_c$ of the driven vibration is different from the resonant frequency $\omega_o$ of the probe, synthesis of vectors of the two vibrations ($\omega_o-\omega_m$, $\omega_o+\omega_m$) corresponding to the sidebands has a combination of the frequency modulation in FIG. 4B and the amplitude modulation in FIG. 4C.

Figure 5A:
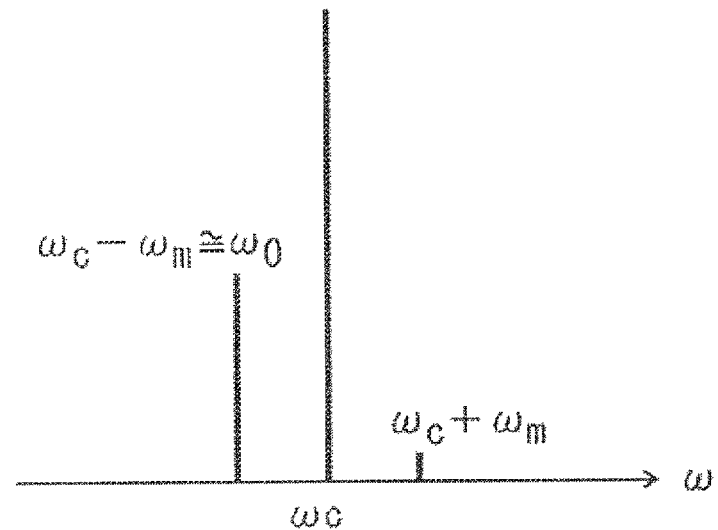
FIG. 5A is a spectrum diagram.

In the spectrum shown in FIG. 5A, the central spectrum is the central frequency of the driven vibration ($\omega_c$). On both sides of $\omega_c$, two sidebands ($\omega_c-\omega_m$, $\omega_c+\omega_m$) by the vibrations by the alternating-current magnetic field generated by the alternating-current magnetic field generating device appear. By choosing $\omega_c-\omega_m$ such that $\omega_c-\omega_m$ is same (or almost same) as the resonant frequency $\omega_o$, it is possible to increase the intensity of the sideband of $\omega_c-\omega_m$ and make the intensity of the sideband of $\omega_c+\omega_m$ negligible.

Figure 5B:
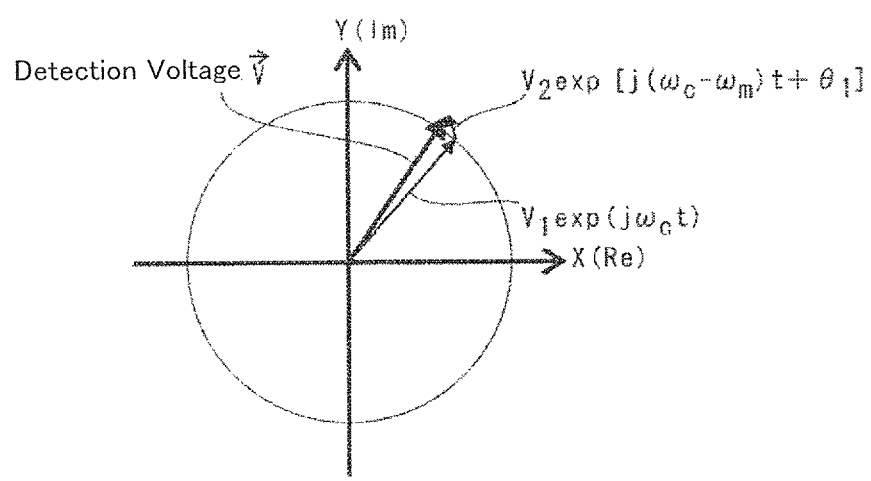
FIG. 5B is a vector diagram to show relationship between a central frequency of driven vibration (central spectrum) and frequencies caused by the alternating-current magnetic field generated by the alternating-current magnetic field generating device (sidebands)

FIG. 5B is a vector diagram corresponding to the spectrum shown in FIG. 5, the vector diagram showing a relationship between the central frequency of the driven vibration (central spectrum) and the frequencies (sidebands) derived from the alternating-current magnetic field generated by the alternating-current magnetic field generating device 5.

In FIG. 5B, the vector corresponding to the central spectrum is represented by $$V_1 \exp(j\omega_c t)$$

and the vector of the vibration corresponding to the sideband of $\omega_o-\omega_m$ (uniform speed rotation vector) is represented by $$V_2 \exp[j\{(\omega_c-\omega_m)t+\theta_1\}].$$

Synthetic vector V to be detected is departed from the trajectory of the vector of the driven vibration (uniform speed rotation vector).

In this case, synthesis of the vectors of the vibrations corresponding to the sidebands changes the frequency and amplitude of the vector of the driven vibration are.

The demodulator 14 includes an alternating magnetic force signal demodulator 141 and a demodulated signal processing device 142. The alternating magnetic force signal demodulator 141 demodulates (by frequency or amplitude), from detection signal of the vibration sensor 13, a magnetic signal corresponding to an alternating-current magnetic field at the position of the probe 111.

The demodulated signal processing device 142 separates the demodulated magnetic signal into two magnetic field components having phase difference of 90°.

The scanning mechanism 15 scans (two dimensionally or three dimensionally) the space where the alternating-current magnetic field exists by means of the probe 111. The scanning mechanism 15 can be configured such that it moves the cantilever 11 or it moves the alternating-current magnetic field generating device 5.

The data storage 16 stores, as an initial data with its phase unchanged, the two separate signal components orthogonal to each other and having phase difference of 90° for each coordinate of the space, wherein the two separate signal components are obtained by scanning the space where the alternating-current magnetic field exists by means of the scanning mechanism 15.

The modulated data generator 17 recalls the initial data from the data storage 16 and generates a plurality of data by modifying the phase of the initial data.

The image display device 18 displays an image of magnetic field distribution based on the data of each coordinate of the scanning space generated by the modulated data generator 17. The image display device 18 can also display an image of magnetic field distribution based on the initial data stored in the data storage 16.

The image display device 18 can, for example, display the image with a range of brightness (density or luminance) having 2N+1 steps from 0 that is the minimum to 2N (N is a positive integer) that is the maximum. In this case, the image display device 18 defines the brightness as "2N" when the intensity of the magnetic field is maximum upward, as "N" when the intensity of the magnetic field is zero, and as "0" when the intensity of the magnetic field is maximum downward, and allocates the 2N+1 steps of the brightness to the intensity of the magnetic field including direction, and thereby generates an image of magnetic field distribution.

By observing the image of magnetic field distribution visually or by software, it is possible to obtain a magnetic profile of the alternating-current magnetic field generating device 5 and a magnetic profile of the space where the alternating-current magnetic field generated by the alternating-current magnetic field generating device 5 exists.

Figure 3:
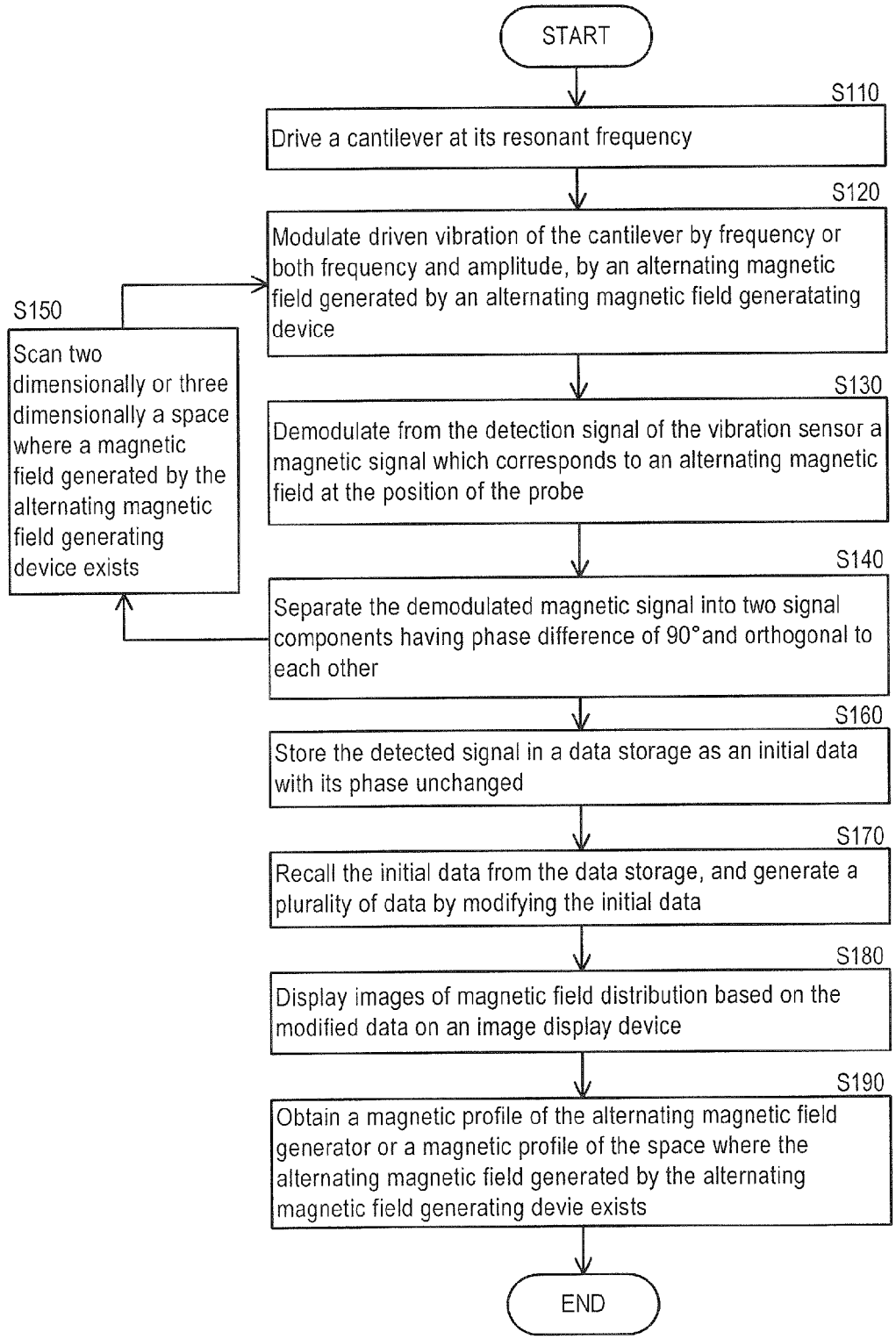
FIG. 3 is a flowchart showing an embodiment of a method for measuring magnetic profile of the present invention.

FIG. 3 is a flowchart to show an embodiment of the method for measuring a magnetic profile of the present invention.

Since the method for measuring a magnetic profile of FIG. 3 is carried out by means of the magnetic profile measuring device 1 of FIG. 2, the operation of the magnetic profile measuring device 1 of FIG. 2 will be hereinafter mainly explained referring to the flowchart of FIG. 3.

The alternating-current magnetic field generating device 5 includes a signal generator 51 and a magnetic coil 52 equipped with a magnetic material (for example, a magnetic recording head), and the signal generator 51 drives the magnetic coil 52 by an alternating-current voltage V represented by Formula (1).

$$V = V_{01} \cos(\omega t) \quad (1)$$

$V_{01}$ of Formula (1) is the amplitude of the alternating-current voltage. The alternating-current voltage applies an alternating-current I represented by Formula (2) to the winding of the magnetic coil 52.

$$I = I_{01} \cos(\omega t - \theta_{d1}) \quad (2)$$

$I_{01}$ in Formula (2) is the amplitude of the alternating current. A delay angle $\theta_{d1}$ is determined by values of resistance, inductance and the like of an electric circuit which composes the magnetic coil (magnetic recording head) having the magnetic material.

By the current $I_{01}$ in Formula (2), the alternating-current magnetic field generating device generates a magnetic field (perpendicular magnetic field component $H_p$) represented by Formula (3) on a reference surface of the magnetic coil 52 (in this embodiment, a sliding surface of a magnetic recording head: hereinafter referred to as "reference surface").

$$H_p = H_{01} \cos(\omega t - \theta_{01}) \quad (3)$$

$H_{01}$ in Formula (3) is amplitude of the alternating-current magnetic field, and the magnetic field of the perpendicular magnetic field component $H_p$ becomes maximum with a time delay of $\theta_{01}/\omega$ from the alternating voltage of the signal generator 51.

The delay angle $\theta_{01}$ is a sum of the delay angle $\theta_{d1}$ in Formula (2) and a delay angle $\theta_{d2}$ in the alternating-current magnetic field generating device 5. $\theta_{d2}$ is a delay angle of magnetization response delay caused when an alternating-current magnetic field is applied to a magnetic core material used in the coil of the alternating-current magnetic field generating device 5, etc.

As described above, in the driver 12 the power source 122 drives the piezoelectric element 121, and the cantilever 11 is driven with the frequency generated by the driver 12 (see S110 in FIG. 3).

The driven vibration of the cantilever 11 is modulated by the alternating-current magnetic field generated by the alternating-current magnetic field generating device 5, by frequency or by both frequency and amplitude (see S120 in FIG. 3).

As described above, in the vibration sensor 13, a laser beam is irradiated from the laser 131 to the upper surface of the tip of the cantilever 11, and its reflected light is detected by the photodiode 132. The alternating magnetic force signal demodulator 141 demodulates the signal (alternating-current magnetic field signal) corresponding to the alternating-current magnetic field at the position of the probe 111 from the detection signal of the vibration sensor 13 (see S130 in FIG. 3).

The demodulator 14 separates the demodulated magnetic signal into two signal components orthogonal to each other and having phase difference of 90° (S140 in FIG. 3).

Output F of the alternating magnetic force signal demodulator 141 is represented by Formula (4).

$$F = F_{01} \cos(\omega t - \theta_{02}) \quad (4)$$

$F_{01}$ in Formula (4) is the amplitude of the alternating magnetic force. A delay angle $\theta_{02}$ is an angle in which a delay of detection circuit of the vibration sensor 13 and the like, if any, is added to the delay angle $\theta_{01}$ in Formula (3). Here, when the frequency of the magnetic field generated by the alternating-current magnetic field generating device 5 is low, $\theta_{02}$ becomes almost equal to $\theta_{01}$.

The demodulated alternating magnetic force signal is represented by Formula (5).

$$F_{01}\cos(\omega t - \theta_{02}) = F_{01}\cos(-\theta_{02})\cos(\omega t) - F_{01}\sin(-\theta_{02})\sin(\omega t) \quad (5)$$

$$= F_{01}\cos(-\theta_{02})\cos(\omega t) + F01\sin(-\theta_{02})\cos(\omega t + 90°)$$

The demodulated signal processing device 142 detects amplitude ($F_{01}$) and the delay phase angle ($-\theta_{02}$) of the alternating magnetic force signal demodulated by the alternating magnetic force signal demodulator 141.

Here, when a magnetization component of magnetic moment (magnetization) m of the magnetic material of the magnetic coil 52 of the alternating-current magnetic field generating device 5 in a direction perpendicular to the reference surface is defined as $m_z$ and a magnetization component in a direction parallel to the reference surface is defined as $m_x$, the magnetic moment of the magnetic material is changed by the perpendicular magnetic field component $H_p$ generated by the magnetic coil composing the alternating-current magnetic field generating device and can be represented by Formulae (6A) and (6B).

$$m_z = m_0 \cos(\omega t - \theta_{03}) \quad (6A)$$

$$m_x = m_0 \cos(\omega t - \theta_{03} + 90°) \\ = -m_0 \sin(\omega t - \theta_{03}) \quad (6B)$$

wherein, $m_z$ and $m_x$ has a phase difference of 90°.

A delay angle $\theta_{03}$ is identical to the delay angle $\theta_{01}$ of the magnetic field generated by the alternating-current magnetic field generating device of Formula (3).

The demodulated signal processing device 142 has a lock-in detection mechanism, and separates a magnetic field gradient in the perpendicular direction derived from $m_z$ and a magnetic field gradient in the perpendicular direction derived from $m_x$ (see S140 in FIG. 3).

This makes it possible to continuously observe time-dependent change of the perpendicular magnetic field gradient $$H_{01} \cos(\theta): 0° \leq \theta \leq 360°$$

associated with the magnetization rotation of the magnetic moment m of the magnetic material composing the alternating-current magnetic field generating device 5.

$F_{01} \cos(-\theta_{02})$ in Formula (5) having the phase delay of $\theta_{02}$ from the phase angle $\theta_{01}$ and amplitude $F_{01}$ and the signal demodulator 51 of the alternating-current magnetic field generating device 5 corresponds to the perpendicular magnetic field gradient component $(\partial Hz/\partial z)\cos(-\theta_{02})$ generated by the component $m_z$ of the magnetic moment m of the magnetic material configuring the alternating-current magnetic field generating device 5 which component is in a direction perpendicular to the reference surface.

$F_{01} \sin(-\theta_{02})$ having a phase shifted forward by 90° corresponds to the perpendicular magnetic field gradient component $(\partial Hz/\partial z)\sin(-\theta_{02})$ generated by the component $m_x$ of the magnetic moment m of the magnetic material configuring the alternating-current magnetic field generating device 5 which component is in a direction parallel to the reference surface.

The scanning mechanism 15 carries out two-dimensional or three-dimensional scanning in the space where the magnetic field generated by the alternating-current magnetic field generating device 5 exists by means of the probe 111 of the cantilever 11 (see S150 in FIG. 3).

Scanning speed of the scanning mechanism 15 is slow enough to be neglected when alternating magnetic force signal demodulator 141 demodulates the alternating magnetic force signal. In this embodiment, the scanning mechanism 15 is configured to carry out two-dimensional scanning of the alternating-current magnetic field generating device 5.

The data storage 16 stores, as described above, these signals as an initial data with its phase unchanged (S160 in FIG. 3).

The modulated data generator 17 recalls the initial data from the data storage 16 and generates a plurality of data by modifying the phase of the initial data (S170 in FIG. 3).

Images of magnetic field distribution based on the data generated by the modified data generator 17 are displayed on the image display device 18 (S180).

By observing these images of magnetic field distribution visually or by software, it is possible to obtain a magnetic profile of the alternating-current magnetic field generating device 5 or a magnetic profile of the space where the alternating-current magnetic field generated by the alternating-current magnetic field generating device 5 exists (S190 in FIG. 3).

Figure 6:
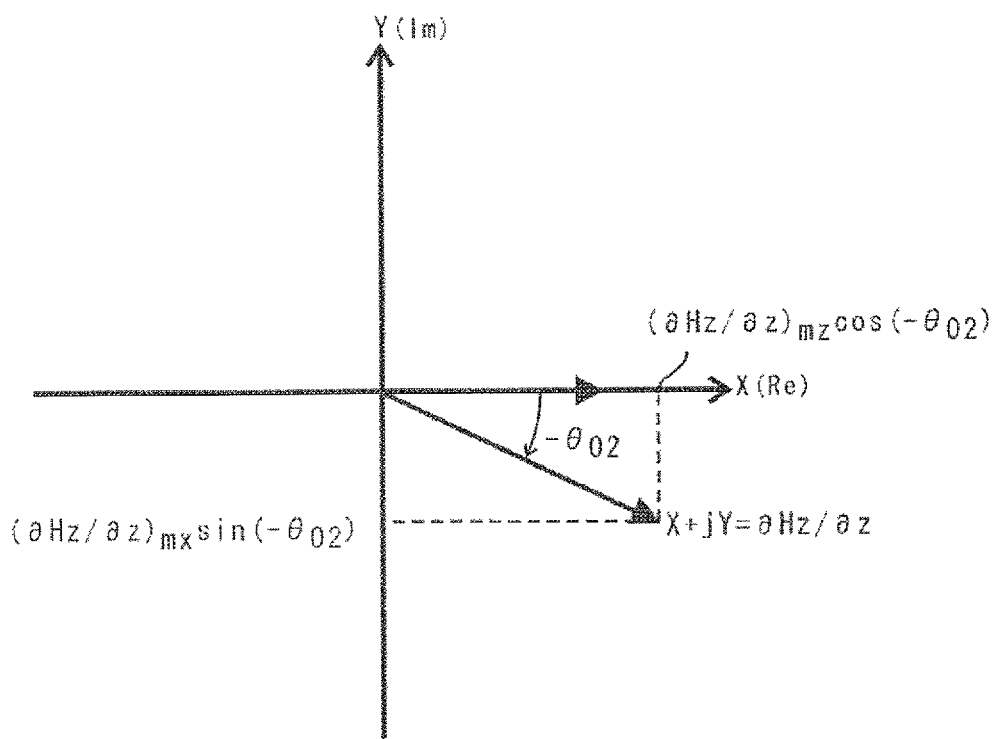
FIG. 6 is a figure for supplemental explanation of a phase of an initial data, the view showing a processing in an embodiment of the magnetic profile measuring device and an embodiment of the method for measuring the magnetic profile of the present invention.
Figure 7:
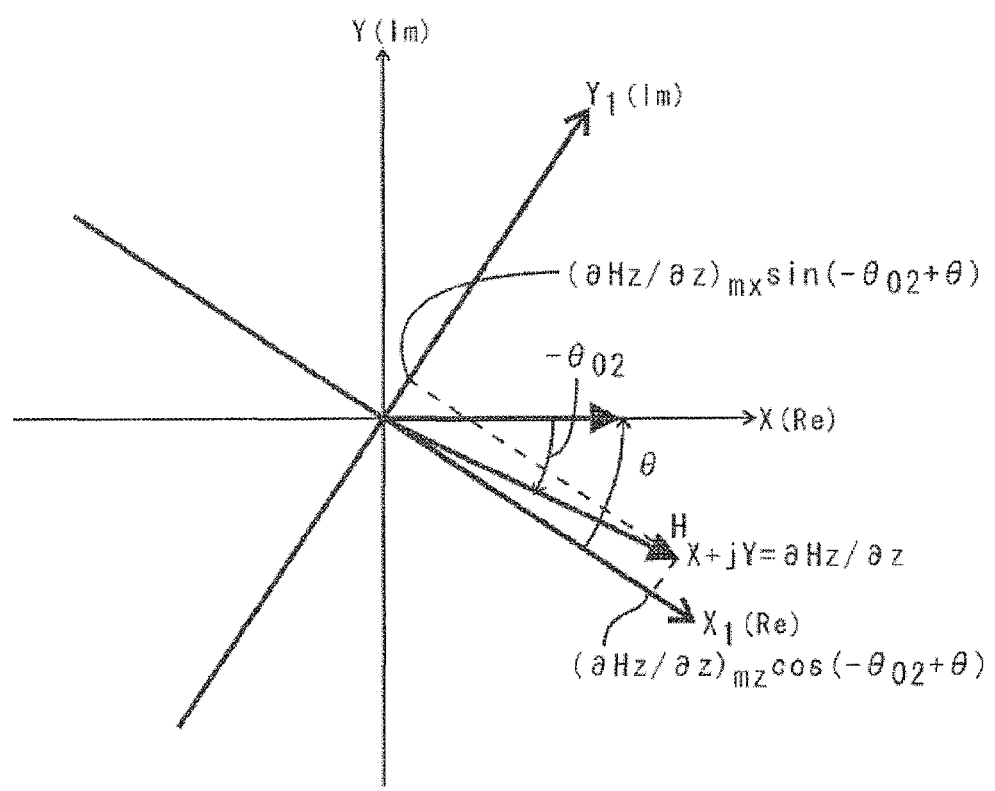
FIG. 7 is figure for supplemental explanation of a phase after phase adjustment, the view showing a processing in embodiments of the magnetic profile measuring device and the method for measuring the magnetic profile of the present invention.

FIGS. 6 and 7 are figures for supplemental explanation of the above process.

The vector diagram of FIG. 6 shown by X-Y coordinate system shows the phase of the initial data (initial phase).

In FIG. 6, the magnetic force gradient vector $(\partial Hz/\partial z)$ is a sum of the magnetic force gradient $(\partial Hz/\partial z)_{mz}$ generated by the component $m_z$ of the magnetic moment m of the magnetic material of the alternating-current magnetic field generating device 5 which component is in the direction perpendicular to the reference surface and the magnetic force gradient $(\partial Hz/\partial z)_{mx}$ generated by the component $m_x$ in the direction parallel to the reference surface, and is represented by Formula (7).

$$X+jY=(\partial Hz/\partial z)_{mz}\cos(-\theta_{02})+j(\partial Hz/\partial z)_{mx}\sin(-\theta_{02})$$

that is, $$X=(\partial Hz/\partial z)_{mz}\cos(-\theta_{02})$$

$$Y=(\partial Hz/\partial z)_{mx}\sin(-\theta_{02}) \quad (7).$$

The vector diagram of FIG. 7 shown by $X_1$-$Y_1$ coordinate system is a vector diagram in which the X-Y coordinate system of FIG. 6 is rotated. By visually operating or by software, it is possible to adjust the phase to zero by adding a correction phase angle $\theta$ to the phase $-\theta_{02}$ in Formula (7).

In the $X_1$-$Y_1$ coordinate system, the magnetic force gradient vector is represented by Formula (8).

$$X_1+jY_1=(\partial Hz/\partial z)_{mz}\cos(-\theta_{02}+\theta)+j(\partial Hz/\partial z)_{mx}\sin(-\theta_{02}+\theta)$$

that is, $$X_1=(\partial Hz/\partial z)_{mz}\cos(-\theta_{02}+\theta)$$

$$Y_1=(\partial Hz/\partial z)_{mx}\sin(-\theta_{02}+\theta) \quad (8)$$

The condition for the phase adjustment is represented by Formula (9).

$$\theta=\theta_{02} \quad (9)$$

This makes it possible to separate the magnetic field generated by the component $m_z$ of the magnetic moment m of the magnetic material of the magnetic coil 52 of the alternating-current magnetic field generating device 5 which component is in the direction perpendicular to the reference surface and the magnetic field generated by the component $m_x$ in the direction parallel to the reference surface from each other.

Further, by continuously changing the phase, it is possible to continuously observe the time-dependent change of the perpendicular magnetic field gradient $$(\partial Hz/\partial z)\cos(\theta): 0° \leq \theta \leq 360°$$

associated with the magnetization rotation of the magnetic moment m of the magnetic material of the alternating-current magnetic field generating device 5.

By modifying the correction phase angle θ by an operator visually observing the display or modifying the correction phase angle θ by software to find out an image having maximum brightness or an image having minimum brightness, it is possible to obtain the condition of Formula (9).

In the above example, a phase of a magnetic field H at the position of the probe 111 is identified by finding out an image having maximum brightness (or an image having minimum brightness). However, it is also possible to obtain the phase (and amplitude) of the magnetic field at the position of the probe 111 by finding out an image having maximum brightness difference or an image having minimum brightness difference.

FIGS. 8A and 8B each shows an example of the images of perpendicular magnetic field distribution of a magnetic recording head having the initial phase that is stored in the data storage 16. FIGS. 8A and 8B have a phase difference of 90°.

Figure 9:
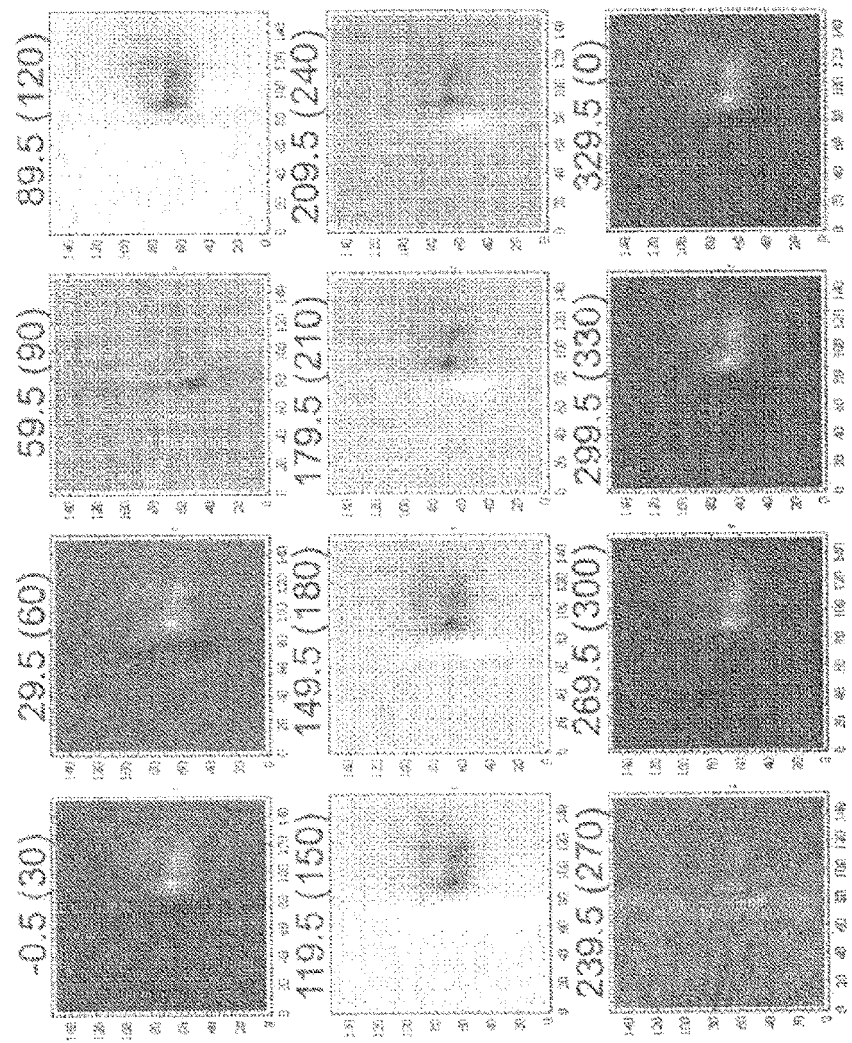
FIG. 9 includes images of perpendicular magnetic field distributions in which phases are sequentially changed, generated from the images of FIGS. 8A and 8B.
Figure 10:
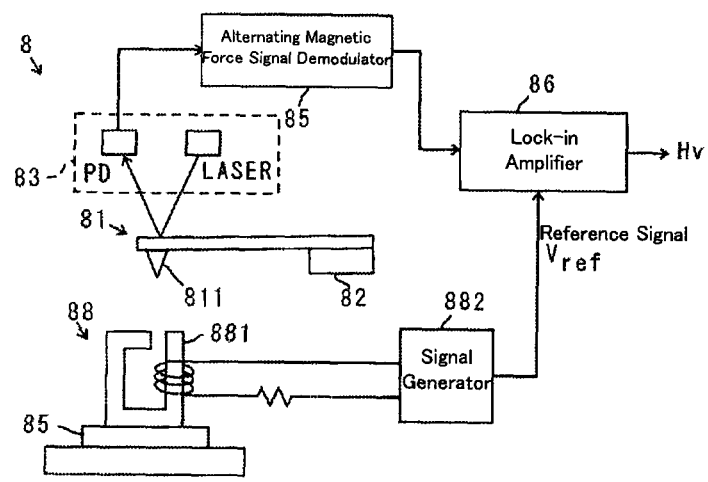
FIG. 10 is a figure to explain a conventional magnetic profile measuring device including a cantilever wherein a magnetized probe is equipped on a tip of the cantilever.

FIG. 9 shows examples of the images of magnetic field distribution of the magnetic recording head generated from the images of FIGS. A and B, wherein their phases are changed.

FIG. 9 shows changes in the images of perpendicular magnetic field distribution associated with the magnetization rotation of the magnetic moment m of the soft magnetic material and shows twelve images of magnetic field distribution in which their phases are changed by every 30° stepwise after adjusting the phase where the magnetic field intensity becomes maximum to zero. For each of the images of magnetic field distribution, phase values are noted. The values are a phase based on the phase of the alternating-current voltage (see above mentioned Formula (1)), and in each parenthesis, a phase in the $X_1$-$Y_1$ coordinate system described above is noted.

As described above, by modifying the correction phase angle while visually observing the images of magnetic field distribution shown on the image display device 18 (or, by modifying the correction phase angle while monitoring the images of magnetic field distribution by software), it is possible to obtain an image of perpendicular magnetic field and an image of in-plane magnetic field.

In FIG. 9, density of the images of perpendicular magnetic field becomes maximum at phase angles of 329.5° (the initial phase is adjusted to 0°) and 149.5° (a phase shifted by 180° forward from the initial phase). Intensity of the perpendicular magnetic field of main magnetic pole part of the magnetic head in the center of image is almost zero at phase angles of 59.5° (the initial phase is adjusted to 90°) and 239.5° (a phase shifted by 270° forward from the initial phase).

DESCRIPTION OF THE REFERENCE NUMERALS

1, 8 magnetic profile measuring device
5 alternating-current magnetic field generating device
11, 81 cantilever
12, 82 driver
13, 83 vibration sensor
14 demodulator
15, 85 scanning mechanism
16 data storage
17 modified data generator
18 image display device
51 signal generator
52 magnetic coil
84 alternating-current magnetic field signal demodulator
86 lock in amplifier
111, 811 probe
121 piezoelectric element
122 power source
131 laser
132 photodiode
141 alternating magnetic force signal demodulator
142 demodulated signal processing device
881 magnetic coil
882 signal generator

The invention claimed is:

1. A magnetic profile measuring device which scans a space where an alternating-current magnetic field generated by an alternating-current magnetic field generating device exists by means of a magnetized probe on a tip of a driven cantilever, detects vibration of the cantilever, and generates an image of magnetic field distribution of the space where the alternating-current magnetic field exists based on results of the detection, the device comprising:
   the cantilever wherein the probe is equipped on the tip of the cantilever;
   a driver driving the cantilever at a resonant frequency of the cantilever or at a frequency close to the resonant frequency of the cantilever;
   a vibration sensor detecting vibration of the probe caused by driven vibration of the cantilever being modulated by the alternating-current magnetic field either by frequency or by both frequency and amplitude;
   a demodulator demodulating from a detection signal of the vibration sensor a magnetic signal which corresponds to an alternating-current magnetic field at the position of the probe, and detecting the demodulated magnetic signal as (A) two separate signal components having phase difference of 90° and being orthogonal to each other or as (B) amplitude and a phase of the magnetic field at the position of the probe;
   a scanning mechanism scanning a space where the alternating-current magnetic field exists by means of the probe;
   a data storage storing an initial data for each coordinate of the space wherein the initial data is (A) the two separate signal components orthogonal to each other or (B) the amplitude and phase of the magnetic field, and wherein the initial data is obtained by scanning the space where the alternating-current magnetic field exists by means of the scanning mechanism, and wherein the initial data is stored with the phase of the initial data unchanged;
   a modified data generator recalling the initial data from the data storage and generating a plurality of data by modifying the phase of the initial data; and
   an image display device displaying an image of a magnetic field distribution based on data generated for each coordinate of the scanned space by the modified data generator.

2. A method for measuring magnetic profile including scanning a space where an alternating-current magnetic field generated by an alternating-current magnetic field generating device exists by means of a magnetized probe on a tip of a driven cantilever, detecting vibration of the cantilever, and generating an image of magnetic field distribution of the space where the alternating-current magnetic field exists based on results of the detection, the method comprising the steps of:
   driving the cantilever at a resonant frequency of the cantilever or at a frequency close to the resonant frequency of the cantilever, wherein the probe is equipped on the tip of the cantilever (S110);

modulating driven vibration of the cantilever by means of the alternating-current magnetic field either by frequency or by both frequency and amplitude (S120);

detecting vibration of the probe and demodulating from the detection signal a magnetic signal which corresponds to an alternating-current magnetic force occurring between the probe and the alternating-current magnetic field generating device (S130);

detecting the demodulated magnetic signal as (A) two separate signal components which have phase difference of 90° and are orthogonal to each other or as (B) amplitude and a phase of the magnetic field at the position of the probe (S140);

scanning the space where the alternating-current magnetic field exists by means of the probe (S150);

storing an initial data in a data storage for each coordinate of the space wherein the initial data is (A) the two separate signal components orthogonal to each other or (B) the amplitude and phase of the magnetic field, and wherein the initial data is stored with the phase of the initial data unchanged (S160);

recalling the initial data from the data storage and generating a plurality of data by modifying the phase of the initial data (S170);

displaying an image of a magnetic field distribution based on data generated by modifying the phase of the initial data, on a image display device (S180); and measuring the magnetic profile of the space where the alternating-current magnetic field generated by the alternating-current magnetic field generating device exists based on each image of magnetic field distribution displayed on the image display device (S190).

3. The method for measuring magnetic profile according to claim 2, comprising the steps of:

modifying the phase of the image of magnetic field distribution having the same phase as the phase of the initial data stored in the data storage, and thereby generating a plurality of images of magnetic field distribution which have different phases; and identifying among the plurality of images of magnetic field distribution an image of magnetic field distribution which has (X) maximum or minimum brightness of the image of magnetic field distribution of the space where the alternating-current magnetic field exists or (Y) maximum or minimum brightness difference of the image of magnetic field distribution of the space where the alternating-current magnetic field exists.

* * * * *